(12) United States Patent
Hara et al.

(10) Patent No.: US 7,307,185 B2
(45) Date of Patent: Dec. 11, 2007

(54) PROCESS FOR PRODUCING OPTICALLY ACTIVE FLUOROCHEMICAL

(75) Inventors: Shoji Hara, Hokkaido (JP); Tsuyoshi Fukuhara, Hokkaido (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/591,698

(22) PCT Filed: Mar. 2, 2005

(86) PCT No.: PCT/JP2005/003480

§ 371 (c)(1),
(2), (4) Date: Sep. 5, 2006

(87) PCT Pub. No.: WO2005/085171

PCT Pub. Date: Sep. 15, 2005

(65) Prior Publication Data

US 2007/0191631 A1    Aug. 16, 2007

(30) Foreign Application Priority Data

Mar. 4, 2004    (JP) .............................. 2004-061202

(51) Int. Cl.
*C07C 69/63* (2006.01)
*C07C 31/34* (2006.01)
(52) U.S. Cl. ...................... 560/226; 568/842
(58) Field of Classification Search ............... None
See application file for complete search history.

(56) References Cited

U.S. PATENT DOCUMENTS 5,276,218 A    1/1994 Bohm et al.

FOREIGN PATENT DOCUMENTS

| JP | 01-228927 | 9/1989 |
|----|-----------|--------|
| JP | 03-184929 | 8/1991 |
| JP | 04-234333 | 8/1992 |

OTHER PUBLICATIONS

Shellhamer, Dale F. et al, "Reaction of diethylaminosulfur trifluoride with diols", 1995, J. Chem. Soc. Perkin Trans 2, 861-866.*

* cited by examiner

*Primary Examiner*—Yvonne Eyler
*Assistant Examiner*—Jennifer Y Cho
(74) *Attorney, Agent, or Firm*—Antonelli, Terry, Stout & Kraus, LLP.

(57) ABSTRACT

The present invention provides a process for producing an optically active fluoro compound represented by formula (3) through reaction between a specific fluoroamine and an optically active diol; and a process for producing an optically active fluoroalcohol through hydrolysis of the optically active fluoro compound. According to the process of the present invention, such optically active fluoro compounds and optically active fluoroalcohols can be produced at high optical purity and high yield in a simple manner. Such optically active fluoroalcohols are a useful source for producing drugs, pesticides, and other functional chemicals

[F1]

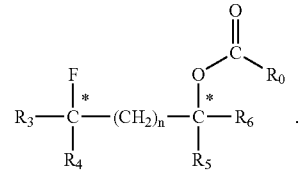

(3)

6 Claims, No Drawings

PROCESS FOR PRODUCING OPTICALLY ACTIVE FLUOROCHEMICAL

TECHNICAL FIELD

The present invention relates to a process for producing an optically active fluoro compound and, more particularly, to a process for selectively producing a monofluoro compound concomitant esterification of a hydroxy group of an optically active diol. The invention also relates to a process for producing an optically active fluoroalcohol from the monofluoro compound. Such optically active fluoro compounds; for example, optically active fluoroalcohol (i.e., fluorohydrin), are a useful source for producing drugs, pesticides, and other functional chemicals.

BACKGROUND ART

Fluoroalcohol is known to be readily synthesized by treating an epoxy compound with HF, HF/pyridine, $KHF_2$, or a similar agent (Non-Patent Documents 1 and 2). However, in the case where an optically active fluoroalcohol in which a fluorine atom is bound to an asymmetric carbon atom is produced, selective production of a desired optical isomer is difficult through employment of the above method, and the product is an isomer mixture. A desired optical isomer of interest can be separated from the mixture through an intricate purification operation such as optical resolution. Thus, a high-optical-purity final product is difficult to obtain at high yield.

A fluorine atom can be introduced to a specific site of an organic compound through a known method employing a fluorinating agent. Such a fluorinating agent is categorized into two types. One is an electrophilic fluorinating agent formally generating a fluorine cation, and the other is a nucleophilic fluorinating agent generating a fluoride anion. A variety of compounds such as HF are known to be nucleophilic fluorinating agents. Particularly when a compound such as diethylaminosulfur trifluoride (DAST) or 2,2-difluoro-1,3-dimethylimidazolidine (DFI) is reacted with an alcohol, an oxygen atom is known to be readily nucleophilic-substituted by a fluorine atom under mild conditions (Non-Patent Documents 3, 4, and 5).

One conceivable approach for synthesizing an optically active fluoroalcohol is treating an optically active diol serving as a source with the aforementioned fluorinating agent. However, when this approach is employed, selective fluorination of only one hydroxyl group of the diol is difficult to attain, and non-target compounds such as a difluoro compound in which two hydroxyl groups are completely fluorinated are readily formed. Thus, in this context, the approach is not suitable (Non-Patent Document 6 and Patent Document 1).

In order to produce an optically active fluoroalcohol through selective fluorination of a diol, reaction of only one hydroxyl group must be promoted. However, at present, difficulty is often encountered for selective introduction of a protective group. Thus, hitherto, there has never been known a technique for introducing a protective group into one hydroxyl group of a diol and selectively fluorinating the other hydroxyl group thereof, and an optically active fluoroalcohol has been considerably difficult to produce at high optical purity and yield.

Non-Patent Document 1:
  Tetrahedron Letters, vol. 31, No. 49, 1990, pp 7209-7212
Non-Patent Document 2:
  Journal of Fluorine Chemistry, vol. 16, 1980, pp 540-541
Non-Patent Document 3:
  Journal of Organic Chemistry, vol. 40, No. 5, 1975, pp 574-578
Non-Patent Document 4:
  Fine Chemical, vol. 31, No. 10 (2002) pp 5-12
Non-Patent Document 5:
  Chemistry & Chemical Industry, vol. 55, No. 3 (2002), pp 259-262
Non-Patent Document 6:
  Journal of the Chemical Society Perkin Transactions 2, 4, 1995, pp 861-866
Patent Document 1: JP11-181022A

DISCLOSURE OF THE INVENTION

An object of the present invention is to provide a process for producing an optically active fluoro compound selectively from an optically active diol at high optical purity and high yield in a simple manner. The optically active fluoro compound is easily convertible to producing an optically active fluoroalcohol.

The present inventors have carried out extensive studies in order to solve the problems described above have resulted in finding that when an optically active diol serving as a starting material is reacted with a specific fluoroamine under heating or under irradiation with a microwave and/or an electromagnetic wave having a wavelength in the vicinity of a microwave region, the object can be attained; i.e., a desired optically active fluoro compound can be formed at high selectivity. The present invention has been accomplished on the basis of this finding.

According to the process of the present invention, a fluoroamine is reacted with an optically active diol via the $S_N2$ mechanism, whereby there can be produced an optically active fluoro compound in which only one hydroxyl group of the starting optically active diol has been selectively substituted by fluorine and which has an inverted configuration. The other hydroxyl group of the optically active diol is reacted with the fluoroamine, to thereby form an ester bond. That is, a protective group can be introduced to the other hydroxyl group. If required, the thus-produced optically active fluoro compound is subjected to a known treatment such as hydrolysis or transesterification, to thereby readily produce an optically active fluoroalcohol.

Accordingly, the present invention provides the following processes for producing an optically active fluoro compound or an optically active fluoroalcohol.

1. A process for producing an optically active fluoro compound represented by formula (3) characterized in that the process comprises reacting a fluoroamine represented by formula (1) with an optically active diol represented by formula (2):

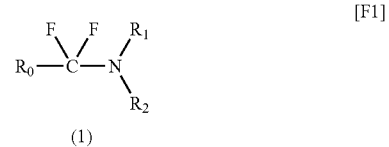

[F1]

(1)

-continued

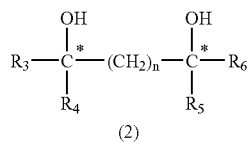

(2)

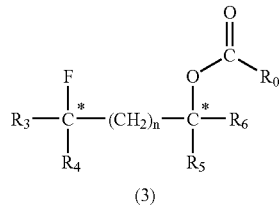

(3)

(wherein each of $R_0$, $R_1$ and $R_2$ of formula (1), which may be identical to or different from one another, represents a hydrogen atom, or an alkyl group or aryl group which may have a substitutent; and two or more groups of $R_0$, $R_1$ and $R_2$ may be linked to form a ring structure; each of $R_3$, $R_4$, $R_5$ and $R_6$ of formula (2) and (3) represents a hydrogen atom, or an alkyl group or aryl group which may have a substitutent; $R_3$ and $R_4$ are different from each other; $R_5$ and $R_6$ are different from each other; the carbon atom to which $R_3$ and $R_4$ are bound is an asymmetric carbon atom; the carbon atom to which $R_5$ and $R_6$ are bound is an asymmetric carbon atom; and n is an integer of 0 to 3).

2. A process for producing an optically active fluoro compound as described in 1 above, wherein $R_0$ of the fluoroamine represented by formula (1) is a 3-methylphenyl group or a 2-methoxyphenyl group, and each of $R_1$ and $R_2$ of the fluoroamine is an ethyl group.

3. A process for producing an optically active fluoro compound as described in 1 or 2 above, wherein the reaction is carried out thermally or under irradiation with a microwave and/or an electromagnetic wave having a wavelength in the vicinity of a microwave region.

4. A process for producing an optically active fluoroalcohol represented by formula (4) characterized in that the process comprises hydrolyzing an optically active fluoro compound which has been produced through a process as recited in any of described in 1 to 3:

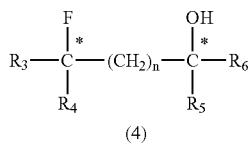

(4)

(wherein $R_3$, $R_4$, $R_5$ and $R_6$ represents a hydrogen atom, or an alkyl group or aryl group which may have a substitutent; $R_3$ and $R_4$ are different from each other; $R_5$ and $R_6$ are different from each other; the carbon atom to which $R_3$ and $R_4$ are bound is an asymmetric carbon atom; the carbon atom to which $R_5$ and $R_6$ are bound is an asymmetric carbon atom; and n is an integer of 0 to 3).

BEST MODES FOR CARRYING OUT THE INVENTION

According to the present invention, the optically active fluoro compound represented by formula (3) is produced through reaction between a fluoroamine represented by formula (1) and an optically active diol represented by formula (2), and the optically active fluoroalcohol represented by formula (4) is produced by hydrolyzing the thus-produced optically active fluoro compound.

In the present invention, each of the groups $R_0$, $R_1$, $R_2$, $R_3$, $R_4$, $R_5$, and $R_6$ in formulas (1) to (4) represents a hydrogen atom, or an alkyl group or aryl group which may have a substitutent. Examples of the alkyl group include methyl, ethyl, propyl, and butyl. Examples of the substitutent which the alkyl group has include an alkyl group and an alkoxy group. Examples of the aryl group include phenyl, methylphenyl, and methoxyphenyl.

The optically active diol serving as a starting material for producing the optically active fluoro compound of the present invention is represented by formula (2).

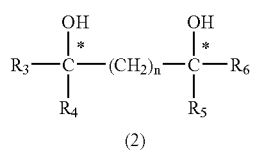

(2)

In formula (2), $R_3$ and $R_4$ are different from each other; $R_5$ and $R_6$ are different from each other; the carbon atom to which $R_3$ and $R_4$ are bound is an asymmetric carbon atom; and the carbon atom to which $R_5$ and $R_6$ are bound is an asymmetric carbon atom.

Specific examples of the optically active diol represented by formula (2) include (2R,3R)-butane-2,3-diol, (2S,3S)-butane-2,3-diol, (2R,4R)-pentane-2,4-diol, (2S,4S)-pentane-2,4-diol, (1R,2R)-diphenylethane-1,2-diol, and (1S,2S)-diphenylethane-1,2-diol. Alternatively, there may be employed a diol compound derived from a sugar through protection of some hydroxyl groups; e.g., 1,2;5,6-O-dicyclohexylidene-D-mannitol.

Examples of the fluoroamine represented by formula (1) include N,N-dimethyl-α,α-difluoromethylamine, N,N-diethyl-α, α-difluoromethylamine, N,N-di(n-propyl)-α,α-difluoromethylamine, N,N-di(isopropyl)-α,α-difluoromethylamine, N,N-di(n-butyl)-α,α-difluoromethylamine, N,N-dimethyl-α,α-difluoroethylamine, N,N-dimethyl-α,α-difluoropropylamine, N,N-dimethylpentafluoroethylamine, N,N-dimethylcyano-α,α-difluoroethylamine, N,N-dimethyl-α, α-difluoro-α-cyclopropylamine, N,N-diethyl-α,α-difluoro(3-methyl)benzylamine, and N,N-diethyl-α,α-difluoro(2-methoxy)benzylamine. These fluoroamine compounds may be synthesized through, for example, a method disclosed in JP2003-64034A.

The reaction between a fluoroamine represented by formula (1) and an optically active diol represented by formula (2) may be carried out in a batch manner, a semi-batch manner, or a continuous manner. The reaction may be carried out simply under thermal conditions or under irradiation with a microwave and/or an electromagnetic wave having a wavelength in the vicinity of a microwave region. In general, the reaction temperature is preferably 200° C. or lower, with room temperature to 150° C. being particularly preferred. The reaction may be carried out under irradiation with a microwave having a frequency of 0.3 to 300 GHz or an electromagnetic wave having a wavelength in the vicinity of a microwave region (e.g., having a frequency of 1 GHz or lower or 30 to 300 GHz). The reaction system may be irradiated with an electromagnetic wave under continuous or intermittent temperature control.

The fluoroamine is preferably employed in an amount of 1 mol or more with respect to 1 mol of hydroxyl groups of the substrate to be reacted (i.e., optically active diol). The amount may be stoichiometerically excessive or deficient.

In the case of thermal reaction, the reaction time is preferably 10 minutes to 360 minutes. In the case where reaction is performed under irradiation with a microwave and/or an electromagnetic wave having a wavelength in the vicinity of a microwave region, the reaction time is preferably 0.1 minutes to 180 minutes. The irradiation may be performed for a longer period of time.

Although no particular solvent is required for the described in above fluorination, a solvent may be employed so as to sufficiently stir the reaction system or to prevent temperature elevation. Preferably, the solvent is inert to a reaction substrate, fluoroamine, and a reaction product. Examples of such solvent include aliphatic hydrocarbons, aromatic hydrocarbons, halo-hydrocarbons, aromatic halo-hydrocarbons, nitrites, and ethers. The solvent is appropriately selected from these examples, and if required, these solvents may be used in combination.

The optically active fluoro compound produced through the above procedure has an ester bond shown in formula (3). Thus, when the optically active fluoro compound is hydrolyzed, the described in above optically active fluoroalcohol represented by formula (4) can be readily produced. The optically active fluoro compound represented by formula (3) may be hydrolyzed through a known hydrolysis method; for example, transesterification or hydrolysis in the presence of a catalyst such as acid, alkali, or a biocatalyst.

EXAMPLES

The present invention will next be described in more detail by way of examples, which should not be construed as limiting the invention thereto.

Prior to description of the Examples, Production Examples of fluoroamine represented by formula (1) will be described as Referential Examples.

Referential Example 1

(Synthesis of N,N-diethyl-α,α-difluoro-(3-methyl)benzylamine)

a) Synthesis of N,N-diethyl-α-chloro-m-toluylamidium chloride

Under nitrogen, a carbon tetrachloride solution (125 g) containing oxalyl chloride (25 g, 0.197 mol) was fed into a three-neck flask (300 mL). While the flask was cooled with ice, N,N-dimethyl-m-toluamide (45 g, 0.236 mol) was added dropwise to the above solution over 20 minutes under stirring. After completion of addition, the mixture was maintained at the same temperature for 10 minutes. The content of the flask was heated to 50° C. and allowed to react for one hour. During reaction, gas generation was observed and, thereafter, a white solid was precipitated. The precipitate was collected through filtration and washed with carbon tetrachloride and n-hexane, followed by drying, to thereby produce 47.5 g of N,N-diethyl-α-chloromethyltoluylamidium chloride (yield: 98%).

b) Synthesis of N,N-diethyl-α,α-difluoro-(3-methyl)benzylamine

To a three-neck flask (500 mL), the above-synthesized N,N-diethyl-α-chloro-m-toluylamidium chloride (25 g, 0.1 mol), spray-dried potassium fluoride (23.5 g, 0.4 mol: product of Morita Chemical Industries, Co., Ltd.), and acetonitrile (250 g) were fed. Under nitrogen, the mixture was allowed to react at a reflux temperature of acetonitrile for 18 hours. After completion of reaction, the reaction mixture was cooled to room temperature, followed by filtration. The filtrate was concentrated by means of an evaporator and distillated, to thereby yield 13 g of N,N-diethyl-α,α-difluoro-(3-methyl)benzylamine (hereinafter referred to as "fluorinating agent A") (yield: 60%).

Referential Example 2

(Synthesis of N,N-diethyl-α,α-difluoro(2-methoxy)benzylamine)

a) Synthesis of 2-methoxy-N,N-diethylbenzamide

A solution of diethylamine (25.8 g, 0.352 mol) in toluene (toluene 30.8 g) was placed in a 200-mL four-neck flask. Under cooling with ice, a solution of 2-methoxybenzoic chloride (20 g, 0.117 mol) in toluene (toluene 10.0 g) was added dropwise gradually in order to prevent sudden surge of heat. After completion of addition of the entire amount of the solution, the formed amine hydrochloride was removed through extraction with water. The thus-obtained toluene layer was dried over $MgSO_4$, and the solvent was vaporized out, to thereby yield 22.8 g of 2-methoxy-N,N-diethylbenzamide (yield: 94%).

b) Synthesis of N,N-diethyl-α-chloro(2-methoxy)phenylamidium chloride

A 200-mL four neck flask was purged with nitrogen, and a 45% solution of oxalyl chloride (oxalyl chloride: 24.5 g, 0.193 mol) in carbon tetrachloride was added to the flask. Under nitrogen, the above-synthesized 2-methoxy-N,N-diethylbenzamide (20.1 g, 0.0965 mol) was added dropwise to the solution at room temperature. During addition, the internal temperature was elevated by 5° C. After completion of addition, the reaction mixture was stirred at 53° C. for 5 hours, whereby the mixture was separated into the two layers. After termination of reaction, the solvent was vaporized out, whereby a viscous liquid was obtained. When the liquid was left to stand in a glove box, a brown solid was precipitated (yield: 26.6 g). The precipitate was washed with hexane and carbon tetrachloride, followed by drying, to thereby yield 21.4 g of N,N-diethyl-α-chloro(2-methoxy)phenylamidium chloride (yield: 80%).

c) Synthesis of N,N-diethyl-α,α-difluoro(2-methoxy)benzylamine

In a glove box, the above-synthesized N,N-diethyl-α-chloro(2-methoxy)phenylamidium chloride (5.0 g, 0.018 mol), acetonitrile (50 g), and spray-dried potassium fluoride (4.4 g, 0.076 mol: product of Morita Chemical Industries, Co., Ltd.) were fed to a three-neck flask (100 mL). Under nitrogen, the mixture was allowed to react at 80° C. for 20 hours. After termination of reaction, the reaction mixture was cooled to room temperature, followed by filtration and washing in the glove box. The-thus obtained solution was concentrated by means of an evaporator and distilled, to thereby yield 3.51 g of N,N-diethyl-α, α-difluoro(2-methoxy)benzylamine (hereinafter referred to as "fluorinating agent B") (yield: 67%).

Thermal stability of the fluoroamine compounds produced in the Referential Examples was evaluated by means of a differential scanning calorimeter (DSC) and an accelerating rate calorimeter (ARC).

Table 1 collectively shows analytical results of fluorinating agents A and B, and relevant data of diethylaminosulfur trifluoride (DAST) and 2,2-difluoro-1,3-dimethylimidazolidine (DFI) reported in the literature (Non-Patent Documents 4 and 5).

TABLE 1

| Fluorinating agent | DSC | | ARC | |
| --- | --- | --- | --- | --- |
| | Exothermal initiation (C. °) | Peak top (° C.) | Heat generated (kJ/g) | Exothermal initiation (C. °) |
| Agent A | 210 | 280 | 0.34 | 180 |
| Agent B | 210 | 255 | 0.24 | 159 |
| DAST | 118 | 149 | 2.1 | 85 |
| DFI | 171 | 225 | 0.66 | 151 |

As is clear from Table 1, as compared with conventional fluorinating agents, fluoroamines (fluorinating agents A and B) produced in the Referential Examples exhibit low heat in DSC generation and high exothermal initiation temperature in ARC. Thus, the fluoroamines have remarkably high thermal stability.

Example 1

Fluorination of (2S,4S)-pentane-2,4-diol (2S,4S)-Pentane-2,4-diol (1 mmol), dioxane (1 mL), and fluorinating agent A (1 mmol) were placed in a Teflon (registered trademark) PFA container and sufficiently mixed. The mixture was placed in a microwave irradiator (product of Sharp, 2.45 GHz, 500 W) and irradiated with a microwave for 10 minutes. After cooling, fluorinating agent A (1 mmol) was further added to the mixture, and the resultant mixture was irradiated with a microwave for another 10 minutes. The reaction mixture was cooled to room temperature, and poured into a saturated aqueous sodium hydrogencarbonate solution. The system was subjected to extraction with ether (40 mL, three times). The ether solution was dried over magnesium sulfate, concentrated, and purified through silica gel column chromatography, whereby (2S,4R)-2-(3-methylbenzoyloxy)-4-fluoropentane, which is a target compound, was produced (yield: 78%, optical purity: 100%).

Comparative Example 1

Fluorination of (2S,4S)-pentane-2,4-diol

The procedure of Example 1 was repeated, except that 2,2-difluoro-1,3-dimethylimidazolidine (DFI; 1 mmol) was used instead of fluorinating agent A. When the mixture was placed in a microwave irradiator (product of Sharp, 2.45 GHz, 500 W) and irradiated with a microwave, reaction was excessively accelerated, and the reaction mixture gushed from the container. Therefore, reaction was not complete.

Example 2

Fluorination of (2R,4R)-pentane-2,4-diol (2R,4R)-Pentane-2,4-diol (1 mmol), a diglyme (1 mL), and fluorinating agent A (2 mmol) were placed in a Teflon (registered trademark) PFA container and the mixture was allowed to react at 100° C. for one hour. The reaction mixture was cooled to room temperature, and poured into a saturated aqueous sodium hydrogencarbonate solution. The system was subjected to extraction with ether (40 mL, three times). The ether solution was dried over magnesium sulfate, concentrated, and purified through silica gel column chromatography, whereby (2R,4S)-2-(3-methylbenzoyloxy)-4-fluoropentane, which is a target compound, was produced (yield: 65%, optical purity: 100%).

Comparative Example 2

Fluorination of (2R,4R)-pentane-2,4-diol (2R,4R)-Pentan-2,4-diol (1 mmol) and dichloromethane (1 mL) were placed in a Teflon (registered trademark) PFA container, and the mixture was cooled with ice. Under nitrogen, N,N-diethylaminosulfur trifluoride (DAST; 1 mmol) serving as a fluorinating agent was added dropwise to the mixture with stirring. After completion of addition, the mixture was allowed to react for 15 minutes. The reaction mixture was poured into a saturated aqueous sodium hydrogencarbonate solution, and the system was subjected to extraction with ether (40 mL, three times). The ether solution was dried over magnesium sulfate, concentrated, and purified through silica gel column chromatography. Optically active fluorohydrin, which is a target compound, was not formed. Instead, racemic 2,4-difluoropentane was produced (yield: 34%).

Example 3

Fluorination of (1R,2R)-1,2-diphenylethane-1,2-diol (1R,2R)-1,2-Diphenylethane-1,2-diol (1 mmol) and fluorinating agent A (2 mmol) were placed in a Teflon (registered trademark) PFA container and the mixture was allowed to react at 140° C. for one hour. The reaction mixture was cooled to room temperature, and poured into a saturated aqueous sodium hydrogencarbonate solution. The system was subjected to extraction with ether (40 mL, three times). The ether solution was dried over magnesium sulfate, concentrated, and purified through silica gel column chromatography, whereby (1R,2S)-1,2-diphenyl-1-(3-methylbenzoyloxy)-2-fluoroethane, which is a target compound, was produced (yield: 83%, optical purity: 100%).

Example 4

Fluorination of (1S,2S)-1,2-diphenylethane-1,2-diol (1S,2S)-1,2-Diphenylethane-1,2-diol (1 mmol) and fluorinating agent B (2 mmol) were placed in a Teflon (registered trademark) PFA container and the mixture was allowed to react at 140° C. for one hour. The reaction mixture was cooled to room temperature, and poured into a saturated aqueous sodium hydrogencarbonate solution. The system was subjected to extraction with ether (40 mL, three times). The ether solution was dried over magnesium sulfate, concentrated, and purified through silica gel column chromatography, whereby (1S,2R)-1,2-diphenyl-1-(2-methoxybenzoyloxy)-2-fluoroethane, which is a target compound, was produced (yield: 87%, optical purity: 100%).

Example 5

Fluorination of (2R,3R)-butane-2,3-diol (2R,3R)-Butane-2,3-diol (1 mmol), a diglyme (1 mL), and fluorinating agent A (2 mmol) were placed in a Teflon (registered trademark) PFA container and the mixture was allowed to react at 100° C. for three hours. The reaction mixture was cooled to room temperature, and poured into a saturated aqueous sodium hydrogencarbonate solution. The system was subjected to extraction with ether (40 mL, three times). The ether solution was dried over magnesium sulfate, concentrated, and purified through silica gel column chromatography, whereby (2R,3S)-2-(3-methylbenzoyloxy)-3-fluorobutane, which is a target compound, was produced (yield: 83%, optical purity: 100%).

Example 6

Fluorination of (2S,3S)-butane-2,3-diol (2S,3S)-Butane-2,3-diol (1 mmol), a diglyme (1 mL), and fluorinating agent B (2 mmol) were placed in a Teflon (registered trademark) PFA container and the mixture was allowed to react at 100° C. for three hours. The reaction mixture was cooled to room temperature, and poured into a saturated aqueous sodium hydrogencarbonate solution. The system was subjected to extraction with ether (40 mL, three times). The ether solution was dried over magnesium sulfate, concentrated, and purified through silica gel column chromatography, whereby (2S,3R)-2-(2-methoxybenzoyloxy)-3-fluorobutane, which is a target compound, was produced (yield: 78%, optical purity: 100%).

Example 7

Fluorination of 1,2;5,6-O-dicyclohexylidene-D-mannitol 1,2;5,6-O-Dicyclohexylidene-D-mannitol (1 mmol), nonane (1 mL), and fluorinating agent A (2 mmol) were placed in a Teflon (registered trademark) PFA container and sufficiently mixed. The mixture was placed in a microwave irradiator (product of Sharp, 2.45 GHz, 500 W) and irradiated with a microwave for 10 minutes. The reaction mixture was cooled to room temperature, and poured into a saturated aqueous sodium hydrogencarbonate solution. The system was subjected to extraction with ether (40 mL, three times). The ether solution was dried over magnesium sulfate, concentrated, and purified through silica gel column chromatography, whereby 1,2;5,6-dicyclohexylidene-3-deoxy-3-fluoro-4-(3-methylbenzoyloxy)mannitol, which is a target compound, was produced (yield: 53%, optical purity: 100%).

Example 8

Hydrolysis of (2S,4R)-2-(3-methylbenzoyloxy)-4-fluoropentane (2S,4R)-2-(3-Methylbenzoyloxy)-4-fluoropentane produced through the method of Example 1 (1 mmol) was mixed with 35% hydrochloric acid (1 mL), and the mixture was stirred overnight. After addition of water to the reaction mixture, the system was subjected to extraction with ether (40 mL, three times). The ether solution was dried over magnesium sulfate, concentrated, and purified through silica gel column chromatography, whereby (2S,4R)-4-fluoropentan-2-ol, which is a target compound, was produced (yield: 95%).

Example 9

Hydrolysis of 1,2;5,6-dicyclohexylidene-3-deoxy-3-fluoro-4-(3-methylbenzoyloxy)mannitol 1,2;5,6-Dicyclohexylidene-3-deoxy-3-fluoro-4-(3-methylbenzoyloxy)mannitol produced through the method of Example 7 (1 mmol) was mixed with 35% hydrochloric acid (1 mL), and the mixture was stirred overnight. After addition of water to the reaction mixture, the system was subjected to extraction with ether (40 mL, three times). The ether solution was dried over magnesium sulfate, concentrated, and purified through silica gel column chromatography, whereby 3-deoxy-3-fluoromannitol[(2R,3R,4S,5R)-4-fluorohexane-1,2,3,5,6-pentanol], which is a target compound, was produced (yield: 92%).

INDUSTRIAL APPLICABILITY

According to the process of the present invention including reaction of an optically active diol with a specific fluoroamine, an optically active fluoro compound in which a diol group has been selectively protected can be produced at high optical purity and high yield in a simple manner.

In addition, according to the present invention, an optically active fluoroalcohol, which is a useful source for producing drugs, pesticides, and other functional chemicals can be produced at high optical purity and high yield in a simple manner; i.e., through hydrolysis of the optically active fluoro compound.

The invention claimed is:

1. A process for producing an optically active fluoro compound represented by formula (3) characterized in that the process comprises reacting a fluoroamine represented by formula (1) with an optically active diol represented by formula (2):

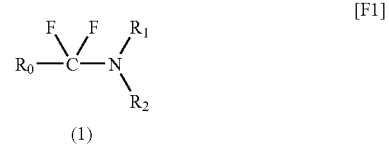

(1)

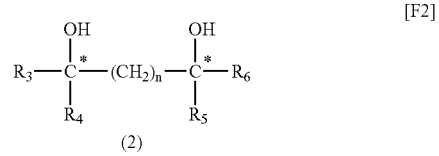

(2)

-continued

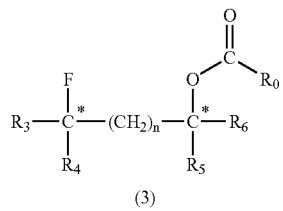

(3)

[F3]

wherein each of $R_0$, $R_1$ and $R_2$, which may be identical to or different from one another, represents a hydrogen atom, or an alkyl group or aryl group which may have a substitutent; and two or more groups of $R_0$, $R_1$ and $R_2$ may be linked to form a ring structure; each of $R_3$, $R_4$, $R_5$ and $R_6$ represents a hydrogen atom, or an alkyl group or aryl group which may have a substitutent; $R_3$ and $R_4$ are different from each other; $R_5$ and $R_6$ are different from each other; the carbon atom to which $R_3$ and $R_4$ are bound is an asymmetric carbon atom; the carbon atom to which $R^5$ and $R^6$ are bound is an asymmetric carbon atom; and n is an integer of 0 to 3.

2. A process for producing an optically active fluoro compound as described in claim 1, wherein $R_0$ of the fluoroamine represented by formula (1) is a 3-methylphenyl group or a 2-methoxyphenyl group, and each of $R_1$ and $R_2$ of the fluoroamine is an ethyl group.

3. A process for producing an optically active fluoro compound as described in claim 1, wherein the reaction is carried out thermally or under irradiation with at least one of a microwave and an electromagnetic wave having a wavelength in the vicinity of a microwave region.

4. A process for producing an optically active fluoroalcohol represented by formula (4) characterized in that the process comprises hydrolyzing an optically active fluoro compound which has been produced through a process as recited in claim 1:

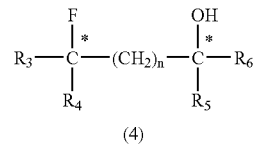

(4)

[F4]

wherein $R_3$, $R_4$, $R_5$ and $R_6$ represents a hydrogen atom, or an alkyl group or aryl group which may have a substitutent; $R_3$ and $R_4$ are different from each other; $R_5$ and $R_6$ are different from each other; the carbon atom to which $R_3$ and $R_4$ are bound is an asymmetric carbon atom; the carbon atom to which $R_5$ and $R_6$ are bound is an asymmetric carbon atom; and n is an integer of 0 to 3.

5. A process for producing an optically active fluoro compound as described in claim 2, wherein the reaction is carried out thermally or under irradiation with at least one of a microwave and an electromagnetic wave having a wavelength in the vicinity of a microwave region.

6. A process for producing an optically active fluoroalcohol represented by formula (4) characterized in that the process comprises hydrolyzing an optically active fluoro compound which has been produced through a process as recited in claim 5:

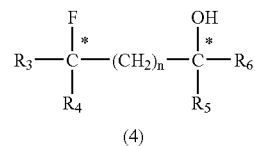

(4)

[F4]

wherein $R_3$, $R_4$, $R_5$ and $R_6$ represents a hydrogen atom, or an alkyl group or aryl group which may have a substitutent; $R_3$ and $R_4$ are different from each other; $R_5$ and $R_6$ are different from each other; the carbon atom to which $R_3$ and $R_4$ are bound is an asymmetric carbon atom; the carbon atom to which $R_5$ and $R_6$ are bound is an asymmetric carbon atom; and n is an integer of 0 to 3.

* * * * *